United States Patent [19]
Ruiz

[11] Patent Number: 6,159,196
[45] Date of Patent: Dec. 12, 2000

[54] METHODS AND APPARATUS FOR TRANSVASCULAR MUSCULAR REVASCULARIZATION AND DRUG DELIVERY

[76] Inventor: Carlos Ruiz, 1747 N. Country La., Pasadena, Calif. 91107

[21] Appl. No.: 09/037,590

[22] Filed: Mar. 9, 1998

[51] Int. Cl.[7] .................................................. A61M 31/00
[52] U.S. Cl. .......................... 604/500; 604/46; 604/264
[58] Field of Search ................................ 604/20, 21, 22, 604/46, 48, 117, 264, 523, 528; 606/167, 170, 172, 181–186; 600/433–435, 585; 607/48

[56] References Cited

U.S. PATENT DOCUMENTS

| | | | |
|---|---|---|---|
| 5,345,940 | 9/1994 | Seward et al. | 128/662.06 |
| 5,454,782 | 10/1995 | Perkins | 604/164 |
| 5,531,676 | 7/1996 | Edwards et al. | 604/22 |

FOREIGN PATENT DOCUMENTS

WO92/10142  6/1992  WIPO .

*Primary Examiner*—Wynn Wood Coggins
*Assistant Examiner*—Kevin C. Sirmons
*Attorney, Agent, or Firm*—Niro, Scavone, Haller & Niro

[57] ABSTRACT

Apparatus and methods for effecting controlled injury to a selected body region to induce muscular revascularization and to provide delivery of drugs and therapeutic agents. A transvascular or muscular revascularization device is provided comprising a stimulator with extended penetrating members and a depth regulator for controlling the extent of penetration through tissue membrane, an outer sheath for retention of the stimulator and selective deployment of the penetrating members of the stimulator, and energy transfer means in communication with the stimulator for effecting a controlled injury to a selected region with directed energy through the penetrating members of the stimulator. A method is further provided for effecting a controlled injury and drug delivery to selected blood vessels or muscle that includes selecting an elongated vascular probe and sheath assembly wherein the vascular probe is formed with a plurality of perforating members to penetrate a membrane wall and a sheath to retain the perforating members of the vascular probe in a retracted position. Upon introduction of the assembly into a selected region, the perforating members of the probe are deployed beyond the outer surface of the sheath to penetrate the selected region which provides localized drug delivery or a controlled injury. A controlled injury may be effected in a localized region such as the myocardium through a coronary vein to provide an angiogenic response that promotes revascularization of the selected muscle region.

7 Claims, 11 Drawing Sheets

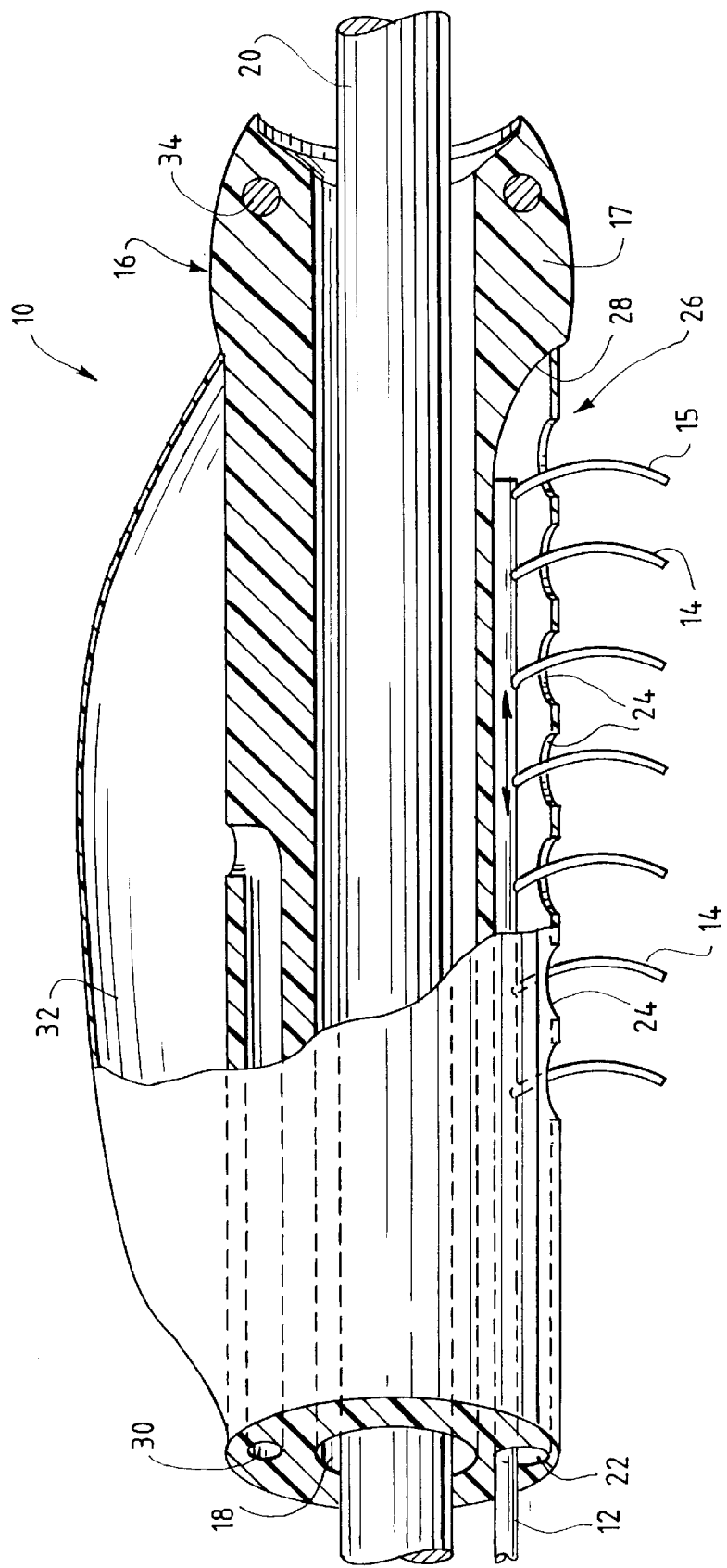

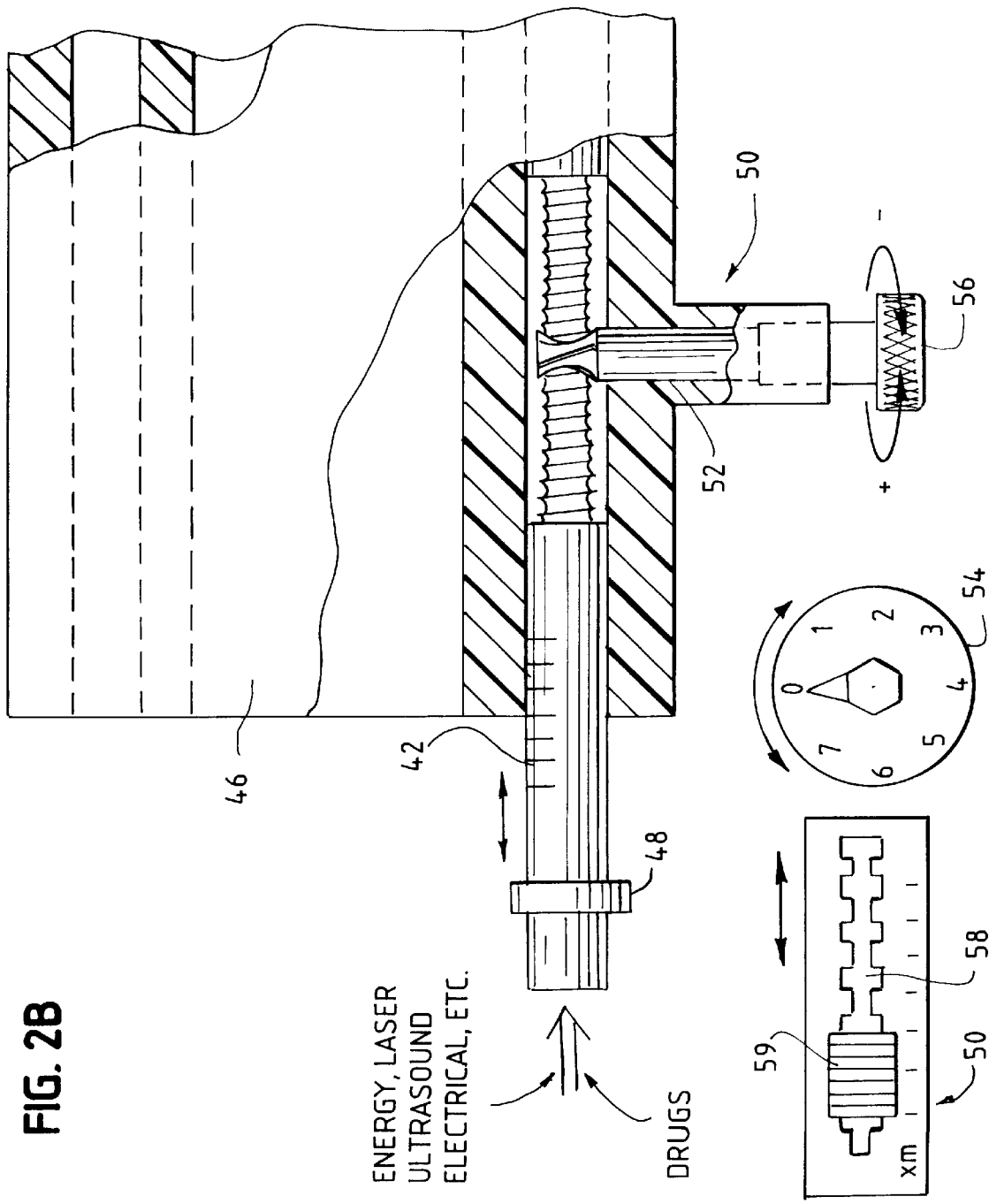

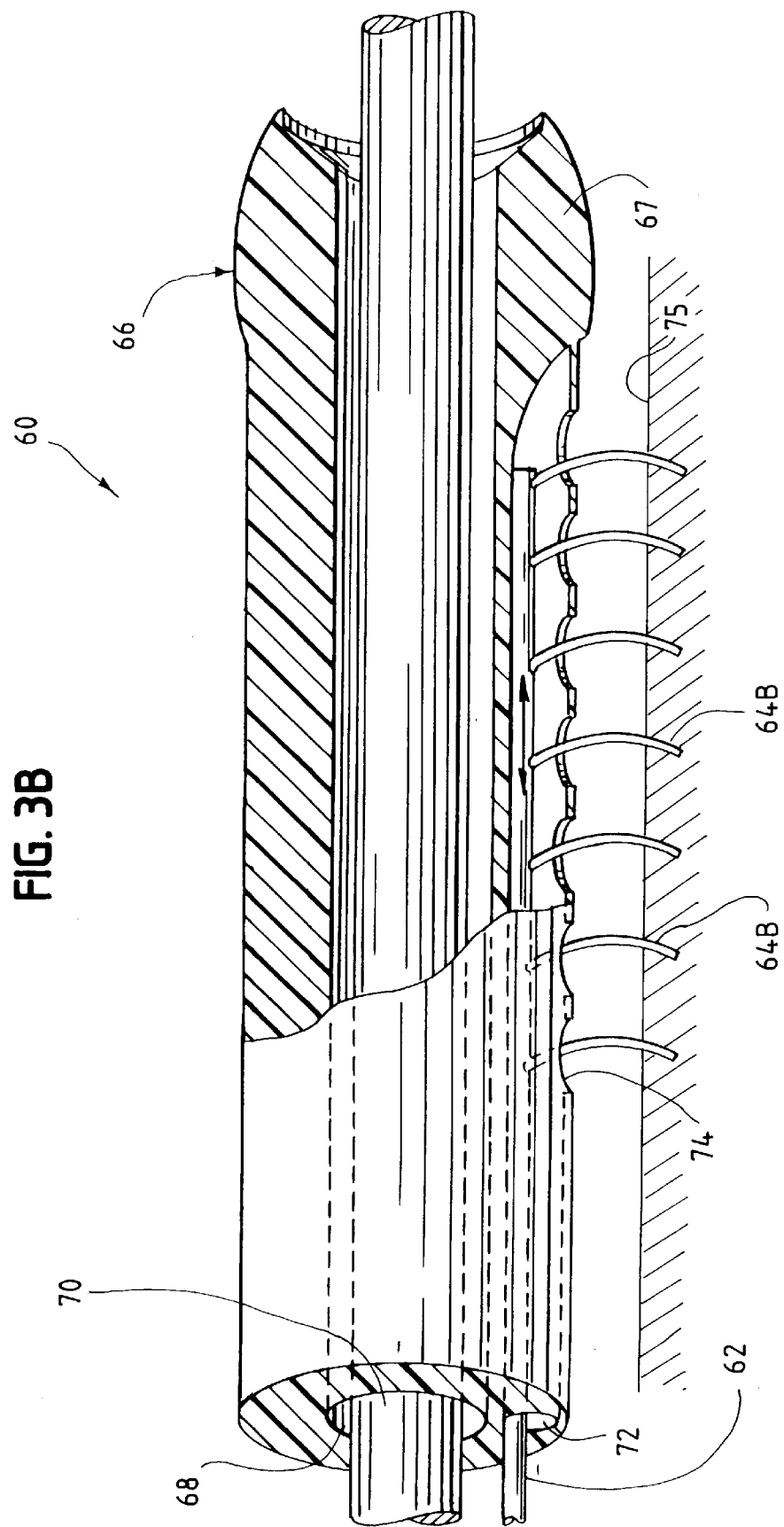

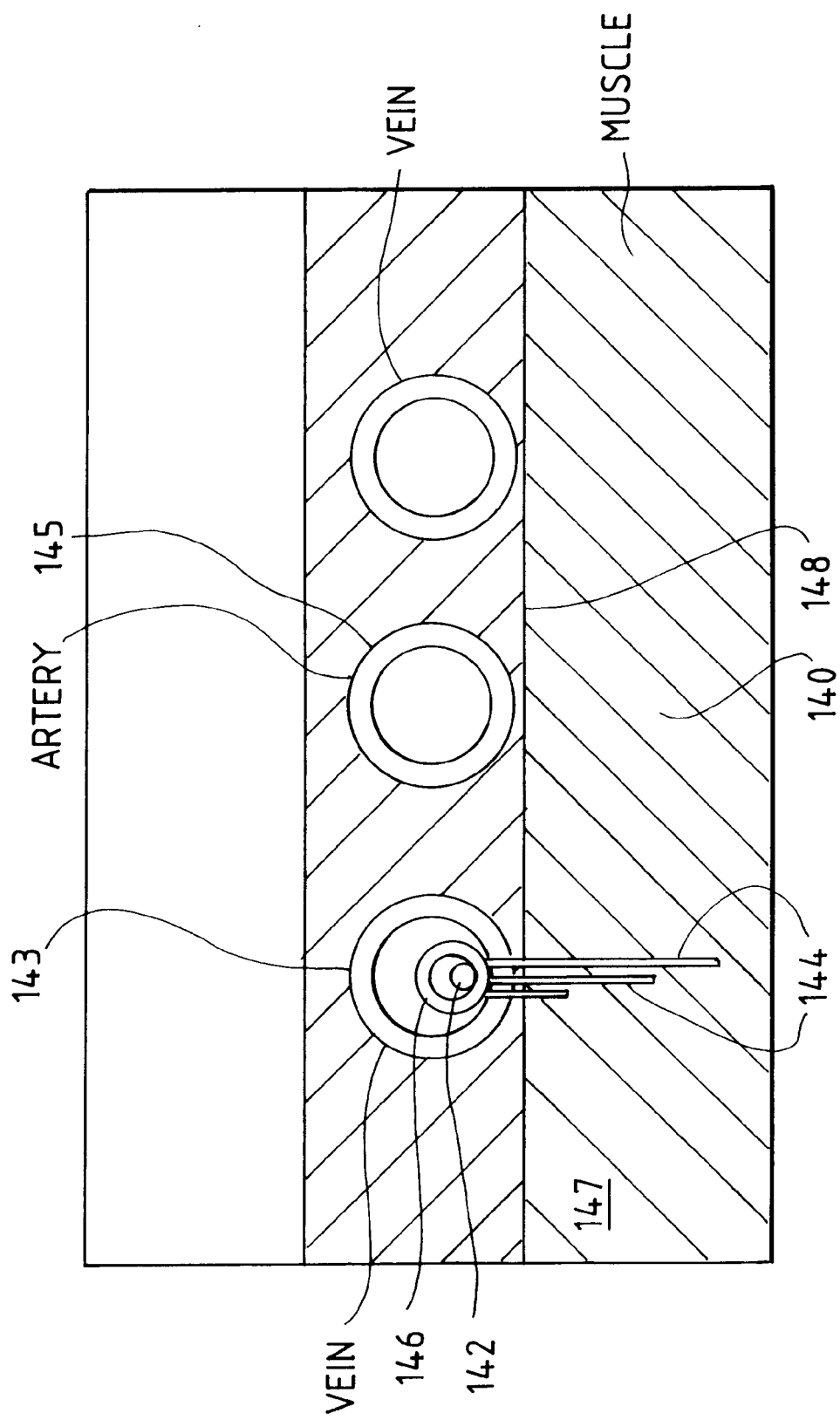

METHODS AND APPARATUS FOR TRANSVASCULAR MUSCULAR REVASCULARIZATION AND DRUG DELIVERY

FIELD OF THE INVENTION

The present invention is generally directed to apparatus and related methods for stimulating muscular revascularization and providing localized drug delivery. More particularly, the invention relates to the transvascular muscular revascularization of selected body regions and the controlled delivery of drugs or therapeutic agents in a highly controlled manner.

BACKGROUND OF THE INVENTION

Angiogenesis is an essential life process by which new blood vessels are formed in response to normal tissue development. The continuous growth of blood vessels or neovascularization provides increased blood circulation throughout various regions of the body. The ability for blood vessels to successfully perform their circulatory function is dependent upon either the existence of relatively unobstructed passageways, or the regeneration or neoformation of new blood vessels. In the past, there has been significant interest in maintaining an adequate blood supply to tissues by removing obstructive material in existing vessels. Many devices and drug therapies have been developed in an effort to eliminate the accumulation of plaque deposited on arterial walls in what is commonly referred to as arteriosclerosis. At the same time, revascularization and the creation of new blood vessels support the changing circulatory needs of the body. It has been observed that neovascularity may be generally achieved in either an artificially induced manner or as a spontaneous bodily reaction. For example, with respect to coronary applications, transmyocardial revascularization has been available for numerous patients in the past when coronary artery bypass grafting procedures were not an available option. During transmyocardial revascularization, multiple channels are generally formed directly in the myocardium to provide ischemic myocardial regions direct access to a source of oxygenated blood. These channels may be formed externally through the epicardial wall with instruments such as laser devices during open chest procedures, or openings may be created percutaneously with devices that access a heart chamber such as the left ventricular endocardium. Various laser apparatus and procedures have been developed to perform these artificially induced neovascularization techniques particularly for end stage coronary artery disease. The patency and effectiveness of these small channels or micro-channels is still being investigated as to the importance of their ability to remain open despite scarring and ensuing fibrosis. The therapeutic benefits and overall effects from these revascularization procedures have not been established with substantial certainty.

The study of angiogenesis and the spontaneous growth of new blood vessels has been studied in depth for many years. Although numerous angiogenic factors have been identified, the precise mechanism by which the body creates new blood vessels is not fully understood. It has been observed that trace amounts of some angiogenic factors exist in normal tissue, but they fail to demonstrate significant angiogenic activity other than in the ordinary growth and development of tissues and organs. In addition, a variety of growth factors and vasoconstrictors demonstrate an ability to promote neovascularization by induced angiogenesis when injected into body regions such as the ischemic limbs of diabetic patients. However, in some instances, the presence of angiogenic factors still fail to promote vascular growth. It has been recently observed that administering certain growth factors provides no added benefit when combined with transmyocardial revascularization. Various systems have been also developed in the past for delivery of these particular drugs or other therapeutic agents to specific target sites including the coronary region. Meanwhile, angiogenic activity has been observed even without the delivery or the presence of any growth factors. More specifically, neovascularization may be initiated during grafting procedures, ischemic conditions or other instances of tissue damage. The delivery of particular drugs and therapeutic agents under the influence of different conditions and stimulus have not provided consistent results in initiating a true angiogenic response.

SUMMARY OF THE INVENTION

The present invention provides apparatus and related methods for effecting a controlled injury to selected vasculature and muscle. The invention further relates to the initiation of transvascular muscular revascularization of selected body regions which may include the delivery of drugs or therapeutic agents. The clinical benefits of revascularization techniques or the initiation of an angiogenic response may be simply the result of a natural body response to an injury. Controlled injury or damage to selected tissue itself may provide sufficient stimulation to initiate an angiogenic response. The actual triggering of an angiogenic response by the body rather than the resultant release and presence of factors associated with angiogenesis has been observed to promote neovascularization. At the same time, the resulting trauma or controlled injury to tissues and organs that achieve neovascularization should not outweigh the benefits offered by their angiogenic affect. Angiogenesis may be further augmented by the local delivery of specific drugs or gene factors that are known to promote neovascularization. A controlled injury to selected vasculature and muscle induces angiogenesis without significant damage to organs or disruption of their function which is often observed with transmyocardial revascularization and other complicated laser surgeries which are highly invasive procedures.

An object of the invention therefore is to provide apparatus and methods that promote muscular revascularization while initiating an angiogenic response. Another object of the invention is directed to the localized delivery of drugs and therapeutic agents such as angiogenic factors to various body sites through venous blood vessels into adjacent tissue. The delivery apparatus and methods may be simultaneously utilized to effect a controlled injury to selected blood vessels and muscle to provide a beneficial tradeoff between initiating an angiogenic response and the accompanying injury.

In a particular embodiment of the invention, a revascularization or tissue stimulating device is provided comprising an elongated probe with perforating members extending away from the probe that are configured to perforate tissue membrane in blood vessels and muscle. The probe may also include a fluid passageway leading to the perforating members of the probe. The perforating members may be detachable tips that include drugs or therapeutic agents. In addition, the stimulating or ablating device may further include an energy source such as a laser and energy transmissive material within the probe for directing or transmitting energy to the perforating members of the probe. A probe sheath may be additionally provided that is formed with a conduit for containment and selective deployment of the perforating members of the elongated probe that extend through openings formed in the sheath. The elongated probe may be slidably mounted within the probe sheath conduit so that the perforating members pass through the sheath openings to extend beyond the outer surface of the sheath.

Another embodiment of the invention includes a catheter system for effecting the controlled injury of a selected body region such as a muscle or blood vessel that comprises an elongated probe formed with a plurality of penetrating extensions that is positioned within the longitudinal lumen of a catheter formed with openings to permit the penetrating extensions of the probe to extend away from the catheter to reach a selected body region. The distal end of the probe lumen may terminate before the distal end of the catheter, and include a tapered surface to restrict further distal movement of the probe relative to the catheter body. The catheter may further include a guidewire lumen and a fixing balloon to provide more accurate placement and stabilization of the penetrating extensions of the probe relative to a body region. The elongated probe may be formed as a micro-needle or otherwise include fluid passageways along the probe and within the penetrating extensions of the probe. The penetrating extensions of the probe may also include detachable tips with embedded drugs or therapeutic agents.

In yet another variation of the invention, an endovascular probe system is provided comprising a guidewire with a longitudinal passageway, a sheath covering such as a catheter that is formed with a guidewire lumen, and an endovascular probe configured for placement within the longitudinal passageway of the guidewire that includes deformable and outwardly biased tips. The endovascular probe may be formed with fluid passageways along the length of the probe in communication with the outer surface of the probe. In addition, the endovascular probe tips may be formed with a penetrating terminal points that are in communication with fluid passageways of the probe. The tips or any other region of the endovascular probe may be detached by a mechanical or an energy release mechanism, and may further include a drug or a therapeutic agent. Alternatively, the drug or therapeutic agent may be positioned within the guidewire openings and released or ejected from the guidewire when the tips of the probe advance through the openings towards the outer surface of the guidewire.

Another object of the invention is to provide a transvascular stimulating device comprising an elongated vascular stimulator that includes a perforating member extending away from the stimulator for effecting a controlled injury in a selected blood vessel region to induce an angiogenic response. An outer conduit such as a guidewire with a central passageway and at least one opening may contain the vascular stimulator and permit passage of at least one perforating member of the vascular stimulator beyond the external conduit surface. The vascular stimulator may include one or more outwardly biased perforating members positioned towards the distal end of the stimulator. Alternatively, the vascular stimulator may include an arcuate segment with a curved surface and a plurality of perforating members that extend through an array of conduit openings beyond the external conduit surface.

An alternate embodiment of the invention provides a muscular revascularization device that includes a muscular stimulator having extended penetrating members for penetrating muscle membrane, and energy transfer means in communication with the muscular stimulator for effecting a controlled injury to a selected muscle region with directed energy through the penetrating members of the stimulator to induce a beneficial angiogenic response and revascularization of the selected region. The revascularization device may further comprise an outer sheath for retention and selective deployment of the penetrating members of the muscular stimulator that are configured to penetrate muscle membrane. A depth regulator may also be included to control the extent of penetration by the penetrating members of the stimulator.

In yet another alternate embodiment, a transvascular muscular revascularization device for penetrating a blood vessel wall is provided comprising an elongated vascular stimulator with energy transfer means for effecting a controlled injury to a selected blood vessel and adjoining muscle region with minimal trauma. The vascular stimulator may also include penetrating members that direct energy such as thermal energy from the energy transfer means into the selected blood vessel wall towards a muscle region. A stimulator sheath may be further added for retention of the penetrating members of the elongated vascular stimulator. The stimulator may further include a depth regulator for selectively controlling deployment of the penetrating members of the stimulator beyond the sheath.

Another aspect of the invention includes a method for effecting a controlled injury and stimulation to selected blood vessels comprising the following steps of selecting an elongated vascular probe and sheath assembly wherein the vascular probe is formed with a plurality of perforating members to penetrate a blood vessel membrane wall, introducing the vascular probe and sheath assembly into a selected blood vessel, slidably moving the vascular probe to deploy the perforating members beyond the outer surface of the sheath to penetrate the selected blood vessel wall in order to produce a localized controlled injury, retracting the perforating members of the probe, and finally removing the vascular probe and sheath assembly from the selected blood vessel. The elongated vascular probe may be configured as an angiogenic vascular stimulator to provide a net beneficial angiogenic response that promotes revascularization by effecting a controlled injury to the wall of a blood vessel such as a vein. The perforating members of the vascular probe may also extend through the blood vessel such as a coronary vein towards adjacent muscle such as the myocardium.

It is a further object of the invention to provide a method for delivering drugs or therapeutic agents comprising the following steps of selecting an elongated delivery probe and sheath assembly wherein the delivery probe is formed with a plurality of probe extensions to penetrate a membrane wall and the sheath is defined by an outer surface and configured to retain the probe extensions of the probe in a retracted position within the sheath, introducing the delivery probe and sheath assembly into a selected body region, slidably moving the delivery probe to deploy the extensions of the probe beyond the outer surface of the sheath to penetrate a membrane wall of the body region, retracting the delivery probe and removing the assembly from the region. A fluid passageway may be formed within the delivery probe and the probe extensions so that drugs or therapeutic agents may be administered through the fluid passageway to the selected body region. The delivery probe extensions may further include detachable tips embedded with therapeutic agents that are deployed by an energy source upon penetration of a membrane wall and retraction of the probe.

BRIEF DESCRIPTION OF THE DRAWINGS

FIG. 1 is a side perspective view of an elongated stimulating probe and catheter system for effecting the controlled injury of a selected body region which includes a fixing balloon for relative positioning.

FIGS. 2A–B are side perspective views of proximal and distal portions of a probe and catheter system that includes a formed lumen within the catheter body for passage of a guidewire, and depth regulators to control the penetration of the probe.

FIGS. 3A–B are perspective views of a stimulator and sheath system which includes a plurality of perforating members for delivery of drugs and therapeutic agents formed along the length of the stimulator that extend through sheath openings beyond the outer surface of the sheath.

FIG. 7 is a simplified diagram shown from a side view of a transvascular stimulator with a depth regulator that determines the extent of penetration and controlled injury of a blood vessel and muscle region with simple mechanical or energy sources.

DETAILED DESCRIPTION OF THE INVENTION

Figure 2A:
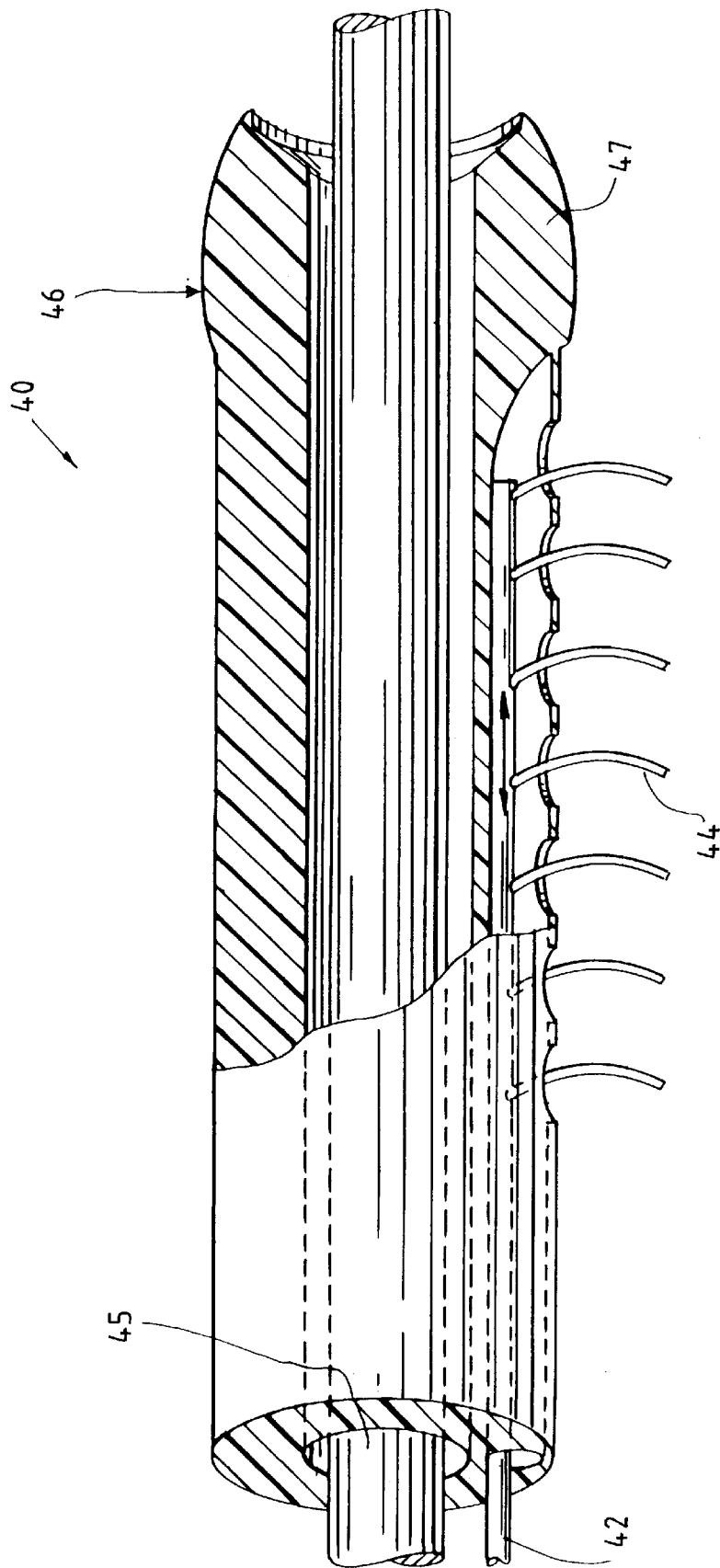

The following detailed description of the invention provides various apparatus and methods for inducing a controlled injury and effecting localized delivery of drugs or therapeutic agents to selected body regions. As shown in FIG. 1, an elongated stimulating probe and catheter system 10 may be formed in accordance with the concepts of the invention for effecting the controlled injury of a selected body region. The elongated probe 12 may be formed with a plurality of penetrating extensions 14 extending away from the probe. The catheter 16 may include single or multiple longitudinal lumens including a first lumen 18 for the passage of a guidewire 20 which may be formed with a wide range of sizes, shapes, and diameters ranging from approximately 0.008 to 0.052 inches or greater. A second longitudinal lumen 22 may be provided for the passage and controlled deployment of the elongated probe 12 that also includes a series of at least one opening 24 formed along the catheter 16 body. The probe lumen openings 24 permit the penetrating extensions 14 of the probe 12 to extend away from the external surface 17 of the catheter 16 to effect a controlled injury at a selected body region. Additionally, the probe lumen 22 may include a distal region 26 formed with a tapered surface 28 to direct a distal penetrating member 15 in a relatively outward direction, and to restrict further distal movement of the probe 12 relative to the catheter 16 body. The catheter system 10 may further include another lumen 30 extending along a portion of the length of the catheter 16 for communication with a fixing or anchoring balloon 32. The fixing balloon 32 may be positioned at a portion of the catheter 16 opposite to an area where the penetrating probe extensions 14 extend beyond the catheter.

The elongated probe 12 may be an intravascular percutaneous device configured for any region of the body including the heart. Other types of applicable devices may include a wide variety of stimulators, multi-pronged needles, microneedles, shaped rods or a variety of modified catheters. Any of these instruments may further include transvascular tips, prongs, penetrating extensions, injectable needles or perforating members that further effect a controlled injury to selected tissue. The probe 12 may include extensions 14 that are formed as needles or prongs with surgical steel or other known materials to perform relatively simple mechanical functions such as the stimulation, penetration or formation of micro-channels at a particular body region. The probe 12 may additionally conduct, direct, or transmit a controlled amount of energy to distal sites through appropriate conduits and materials including optical or light transmitting fibers, radio frequency wires and ultrasonic wires. A selected number of penetrating extensions 14 of the elongated probe 12 may further deliver drugs or therapeutic agents to selected body regions. Moreover, the probe 12 may include longitudinal fluid or open passageways formed along the length of probe including within the penetrating extensions 14 of the probe themselves. As a result, material may be introduced at a proximal region of the probe for ultimate delivery at distal sites in the proximity of the penetrating probe extensions 14. In this manner, the elongated probe 12 may function as a multi-pronged micro-needle. Alternatively, the penetrating extensions of 14 the probe 12 may be formed as detachable tips.

The tips may further include a variety of drugs or therapeutic agents for localized delivery and therapy.

The outer catheter or sheath 16 may similarly vary in size and configuration depending upon particular applications and the design of the probe 12. A 3 to 12 French catheter or micro-catheter may be selected, and may be sized and formed with tapered distal regions to readily pass through a variety of blood vessels including coronary, limbs and cerebral vasculature. The catheter 16 may include any number of lumens or passageways that permit access or the passage of one or more probes, guidewires, fluids, expandable balloons, or any other portion or selected attachment to the catheter. In particular, a passageway 22 within the catheter may facilitate the placement of a probe 12 with deformable perforating extensions 14. The perforating extensions 14 of the probe 12 may be placed in a stored position, and rest below the outer surface 17 of the catheter 16. The distal movement of the probe 12 relative to the catheter 16 may advance the extensions 14 so they protrude beyond the outer surface 17 of the catheter. The perforating extensions 14 may pass through openings or orifices 24 formed along a region of the catheter 16 to reach blood vessel or tissue walls. The extensions 14 may protrude beyond the catheter 16 at various distances depending upon particular applications. The relative size and shape of the probe 12 itself and its perforating extensions 14 may similarly vary according to selected target regions and procedures.

The fixing or anchoring balloon 32 of the catheter 16 may assist in the relative positioning of the apparatus within a blood vessel, body cavity or other selected region of the body. The balloon 32 may assist in maintaining the position of the probe 12 and catheter 16 at a particular site, and more readily permit advancement of the perforating members 14 through the a blood vessel or membrane wall even in the presence of circulating fluid or blood surrounding the region. The guidewire lumen 18 or other lumens in the catheter may of course permit fluid to pass through the region while the balloon 32 occludes the body region. When inflated, the balloon 32 provides a relatively rigid structure so that the perforating members 14 of the probe 12 may be pushed in close contact, or in a relatively close proximity, to a membrane wall. Other alternatives to secure the relative position of the catheter and probe assembly 10 may be alternatively used and positioned opposite the penetrating extensions 14 of the probe and their corresponding openings 24 in the catheter 16 or along any other distal or proximal position along the catheter. A selected portion of the catheter 16 may also include guiding elements 34 for steering or positioning the assembly within a desired location. The catheter 16 tip then may be formed with intravascular ultrasound devices 34 for direct guidance and proper orientation. Other known apparatus and methods for placement of catheter and guidewire devices within the body may be applied to all embodiments of the invention as described herein.

As shown in FIGS. 2A–B, the proximal and distal portions of a stimulator and catheter system 40 may include various components to assist in deployment of the stimulator extensions 44. When the outer surface 47 of the catheter or sheath 46 is maintained in an adjacent or a relatively fixed relationship with a membrane wall, the extent of penetration is more accurately reflected by a depth regulator. As shown in FIG. 2B, a variety of depth regulators or controllers 50 may be selected and positioned in a proximal position or at other locations along the stimulator 42. The depth regulator 50 may be formed as a stopper 48 attached or formed in a relatively proximal or distal portion of the stimulator 42 to prevent further advancement of the stimulator into the sheath or guidewire 46. Alternatively, a threaded advancement guide 52 with a calibrated gauge 54 may be selected as shown in FIG. 2B. By rotating a depth regulating knob 56 which may indicate the extent of penetration in millimeters, the penetrating extensions 44 may either be advanced (+) or retracted (−) relative to the sheath 46. The depth regulators 50 may of course operate separately although they are collectively illustrated in FIG. 2B. For single-handed operability, the depth regulator 50 may further cooperate with a sheath assembly 46 formed with an aperture 58 that is calibrated to measure the advancement of the stimulator or the extension of the perforating members 44 away from the sheath surface into a selected region. A slidable finger pad 59 may be also positioned within a notched aperture 58 that is connected to the stimulator 42. Similarly, the depth regulator 50 may be configured as a spring activated advancement device that includes a biased controlled lever such as those found in mechanical pencils (not shown). By simply depressing the biased lever, the stimulator 42 may be advanced within the sheath 46 and its penetrating members 44 extended beyond the outer surface 47 of the sheath by a preselected distance or millimeter increment. It should be understood that these and other known depth regulating devices may be also applied to all other embodiments of the invention described herein.

The stimulator and catheter system 40 shown in FIGS. 2A–B may be also configured for muscular revascularization system throughout the body. In addition to the physical formation of micro-channels that may permit fluid flow across a penetrated membrane, the apparatus and other aspects of the invention described herein induce an angiogenic response in particular regions of the body such as the heavily emphasized coronary region. An angiogenic response may be induced by the application of certain stimuli and conditions such as tissue injuries, ischemia, grafting or transplant and ablation procedures. Because angiogenesis is observed in these instances when tissue injury has already occurred, vascularity may not significantly increase by further stimulating an already injured site. The occurrence of the injury itself has presumably triggered an angiogenic response. However, in order to augment this response, the present invention may provide stimulation of neighboring tissue, which is relatively healthy, in a controlled manner to further promote angiogenesis. The already affected regions may be stimulated as well to ensure maximum response from the body without significant aggravation to the injury. When direct stimulation of an injured organ or its respective arterial blood vessels is not feasible, the surrounding venous blood vessels may be controllably injured, or otherwise stimulated, by a mechanical or an energy source in order to induce a beneficial angiogenic reaction. Furthermore, when endovascular or percutaneous access to a remote site is desired, a guidewire 45 may assist in the initial placement of the stimulator and catheter system 40 within selected blood vessels around neighboring tissue. Although various organs and exposed muscle may be directly stimulated by the stimulator 42 and its penetrating extension 44, the system 40 is particularly suitable for intravascular applications within arteries and veins such as those found in heart region to promote myocardial revascularization. By properly navigating selected vasculature, almost any region in the body may be reached by either an artery and at least one corresponding vein. Although arteries may be accessed for providing the benefits of the invention to selected portions of the body including the coronary region, venous routes may be preferred. Arteries may be generally described as a relatively high pressure segment of the circulatory system as compared to veins. Most attempts to access arteries present physical difficulties in proper positioning of catheters and similar devices due to the obstructive atherosclerotic characteristics of arterial disease. The body also reacts adversely to disturbances of sensitive arterial wall regions, and may trigger the release of various undesirable factors which lead to other complications such as new atherosclerotic plaques and localized thrombosis. When attempting to access a heart chamber or region as in transmyocardial revascularization procedures, complications may arise such as perforations and lethal arrhythmias. Moreover, arterial access often disturbs normal circulatory functions by the obstructive effect caused by the device itself which may further worsen ischemia. Additional lumens therefore may be added within the revascularization or drug delivery apparatus described herein to permit blood to flow through a region occupied by the apparatus so that interference with normal circulation is minimized when a fixing balloon is expanded within an arterial blood vessel. In any event, the resulting consequences from such procedures which embody the concepts of the invention may be addressed in various manners as known by those skilled in the field.

The revascularization apparatus and methods described herein are particularly beneficial when implemented transvenously to selected regions. As described earlier, arterial or direct access to selected muscle regions such as the myocardium are not the only percutaneous routes available to reach affected areas. The muscular revascularization apparatus and methods provided herein may be adapted for operation within arterial blood vessels or upon organs directly. However, native veins do not develop atherosclerotic obstructive lesions which allows access to virtually any target region of the body through the venous system. Furthermore, the hemodynamics in venous blood vessels also do not present the same risks for bleeding as the relatively high pressure arterial system. The unintended injury to blood vessel walls during the use of high energy apparatus such as lasers are often not as problematic in veins. When selected venous blood vessels are accessed, transvenous muscular angiogenesis may be initiated or induced by simple penetration of the venous wall in a direction towards neighboring muscle. While this form of venous acupuncture may promote revascularization of affected muscle regions, the same apparatus may also be utilized to provide delivery of drugs, or any number of pharmacological or therapeutic agents. In order to enhance the angiogenic response by effecting a controlled injury, a selected probe or stimulator may include penetrating members that carry angiogenic factors such as basic fibroblast growth factor (BFGF), vascular endothelial growth factor (VEFG), vasoconstrictors, or any other agents that are known to promote or to induce an angiogenic response. In addition, the angiogenic effect of the controlled injury through venous blood vessels may be present with a flexible degree of stimulation. Because it is a relatively low pressure system that performs various functions such as drainage, there are reduced difficulties presented when promoting revascularization and less risk of creating encapsulated hematomas. The oxygen requirements of distal muscle regions and the high demands placed on relatively high pressure arterial blood vessels that are even healthy make them less tolerant to trauma or controlled injury, and may not allow the same amount of time to effect drug delivery or a controlled injury that may be available in venous blood vessels. Venous access routes further reduce the imminent consequences in the event of mechanical failure. Because some disclosed applications require relatively small stimulators, their corresponding perforating members may be extremely small and may have reduced durability. In the event perforating members break away from the stimulator, they may become lodged in a venous blood vessel wall and cause relatively inconsequential injury. If perforating members of the probe enter the venous bloodstream, these foreign bodies may be transported to the lung region where again the risk of severe injury is significantly reduced. Because venous blood vessels reach distal sites to the same extent as, if not more than, arterial blood vessels localized inducement of angiogenesis may be consistently achieved in the proximity of selected muscle. Every artery in the body is often accompanied by at least one or two corresponding venous blood vessels. More accessible routes to target sites and muscle regions may be therefore provided through veins to effect transvenous muscular revascularization. The controlled injury in particular areas such as coronary or skeletal muscular regions through selected venous blood vessels may produce an angiogenic response that provides revascularization, but without presenting more risk or causing more damage than the conferred benefits.

Figure 3A:
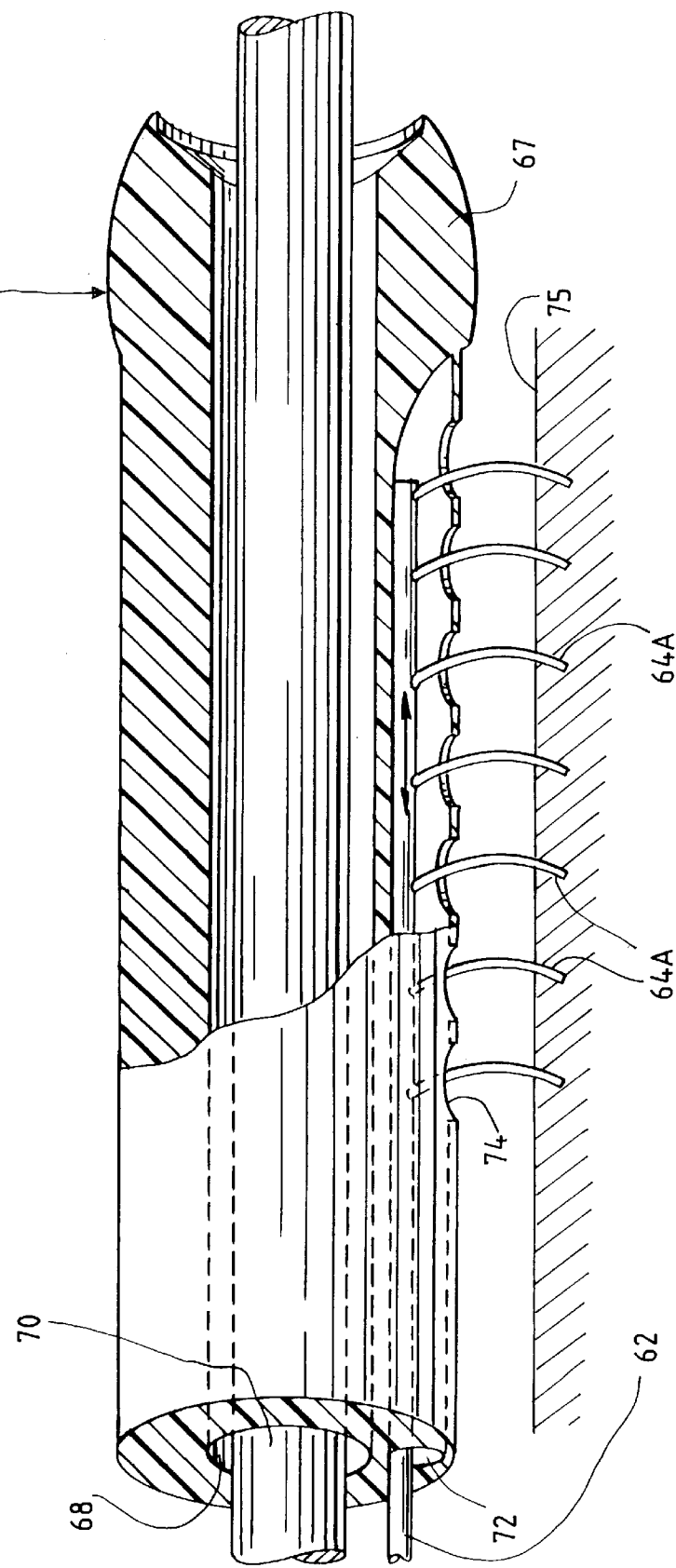

Additional probe and sheath systems 60 formed in accordance with the concepts of the invention are illustrated in FIGS. 3A–B. The plurality of perforating members 64A–B formed along the length of these probes 62 extend through sheath openings or apertures 74 beyond their outer surface 67. The perforating members 64A–B may extend away from an elongated probe 62 to perforate tissue membrane 75, and may be relatively rigid or deformable so as to bend both parallel to and perpendicular to the probe. In addition to promoting revascularization, the probe 62 may be configured for delivery of drugs or therapeutic agents to muscles, blood vessels or both. Although the perforating members 64A–B of the tissue stimulating device may include chemically or genetically treated detachable tips 64A and drugs or therapeutic agents, a fluid or open passageway may be formed within the elongated probe (not shown) and through the perforating members 64B of the probe to provide a micro-needle. In an effort to enhance revascularization of a selected region, stimulation of tissue membranes 75 may be supplemented with the delivery of various known angiogenic factors including basic fibroblast and vascular epithelial growth factors, and other complementary therapeutic agents such as vasoconstrictors. Alternatively, the probe body 62 and extensions 64A–B may include energy transmissive material for delivering energy from a source which may be located at a proximal end of the probe as shown in FIG. 2B. Various forms of energy may be transmitted from an originating source in communication with the probe such as a laser, an ultrasound transducer, radio frequency transmitter, to the perforating members of the probe and beyond the region immediately adjacent the probe sheath 66. The probe 62 may direct energy such as electrical energy through electrical fibers to selected body regions in performing highly localized ablation procedures.

The probe sheath 66 may be formed with a conduit 72 for containment and selective deployment of the perforating members 64A–B of the elongated probe 62. A plurality of openings or orifices 74 of various sizes and shapes may be formed along the outer surface 67 of the sheath 66 that are in communication with the conduit 72. The elongated probe 62 may be slidably mounted within the probe sheath conduit 72 so that perforating members 64A–B may pass through openings 74 of corresponding shapes and sizes to extend beyond the outer surface 67 of the sheath 66. For example, a dual concentric catheter system (not shown) may be selected wherein the outer surface of the relatively inner catheter is formed with perforating members that are selectively deployed through openings by relative movement within the relatively outer catheter. In addition, the probe and sheath system 60 may further include a depth regulator such as those illustrated in FIG. 2B for controlling the extent to which the perforating members 64A–B extend beyond the outer surface 67 of the sheath 66 into a selected target region. A guidewire 70 may be selected and positioned within a lumen to assist in the placement of the probe assembly 60. As described above, the probe 62 may include basic mechanical structures or direct regulated quantities of energy in various forms to stimulate or cause a controlled injury at a selected body region. The apparatus and procedures provided herein cause controlled injuries to blood vessels, muscles or organs that preferably do not outweigh the benefit of their intended or angiogenic effect.

Figure 4:
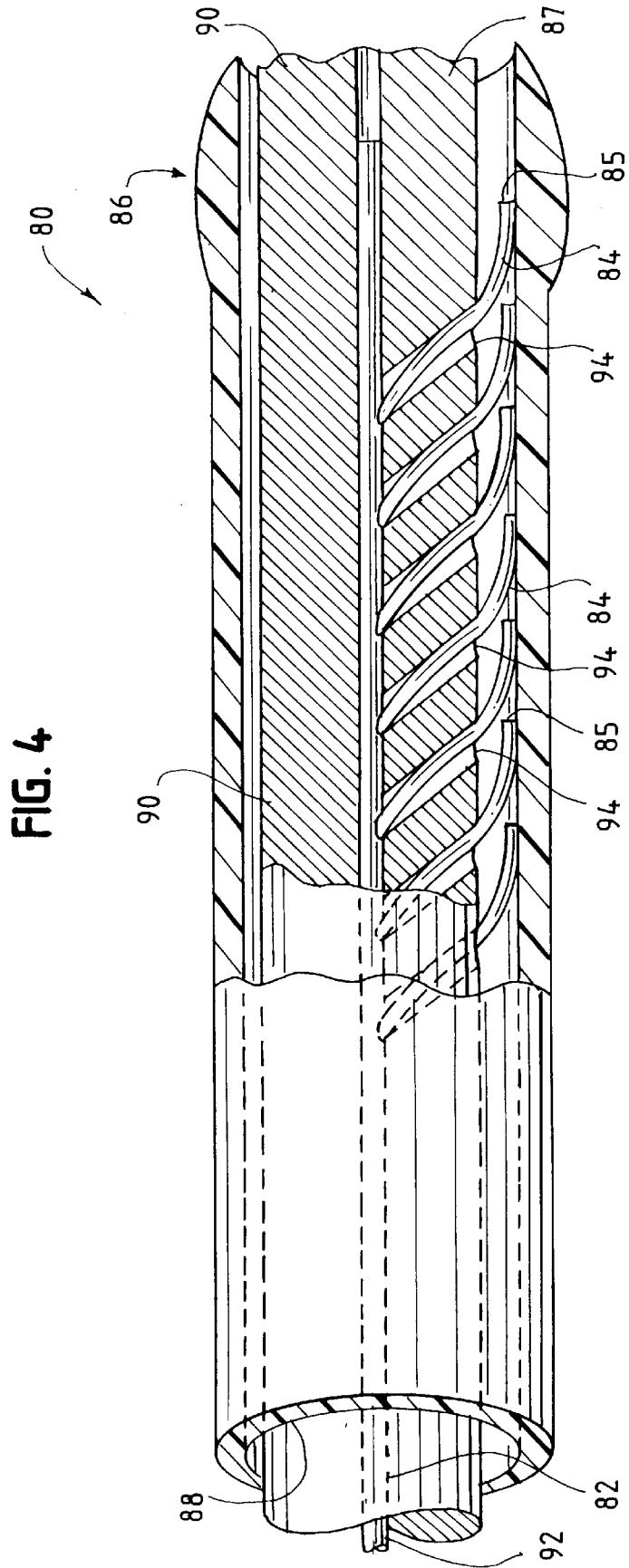
FIG. 4 is a side view of an endovascular stimulating system including a guidewire, sheath covering and an endovascular probe for placement within a passageway formed in the guidewire.

FIG. 4 illustrates another embodiment of the invention that provides an endovascular stimulating system 80 with a probe 82 positioned within the inner core of a stabilizing guidewire 90. As described above, a sheath covering 86 such as a catheter may further assist in the placement and deployment of the probe 82 within a blood vessel such as a coronary vein. As shown in FIG. 4, the endovascular probe system 80 may include a probe 82 configured for placement within a longitudinal passageway 92 in the guidewire 90. The longitudinal passageway 92 formed in the guidewire 90 may terminate before the distal end 89 of the guidewire to restrict further distal movement of the endovascular probe 82 relative to the guidewire. Alternatively, the probe 82 may include a stopper at a proximal portion (not shown) to restrict advancement of the probe tips 84 outside of the guidewire 90 or into a selected body region. In particular applications, the guidewire 90 itself may be sufficient to place and deploy the probe tips 84 without the assistance of a sheath covering 86. The endovascular probe 82 may include at least one deformable and outwardly biased tip 84 to extend away from the longitudinal axis of the probe when displaced from the guidewire passageway 92. The tips 84 may be spaced apart at various distances and be formed of different or similar relative lengths. The guidewire passageway 92 includes at least one opening 94 in communication with the outer surface 87 of the guidewire 90 for passage of a probe tip 84. The endovascular probe 82 may be also formed with fluid passageways along the length of the probe (not shown) that are in communication with the outer surface 87 of the probe so that drugs or therapeutic agents may be delivered and released at a relatively distal region near the probe tips 84. In addition, the tips 84 of the endovascular probe 82 may be formed with penetrating terminal points 85 to penetrate blood vessel linings or other tissue membranes. The endovascular probe tips 82 may be detachable and include chemically or genetically pre-treated polymer portions or other applicable agents for gene therapy (not shown). Various well known mechanisms may be selected to detach the probe tips 84 including those that are activated when various forms of energy such as electrical energy are applied through the probe as shown in FIG. 2B. For example, the tips 84 of the probe 82 may be advanced to penetrate a venous blood wall to reach an adjacent muscle region. An appropriate amount of current may pass through a particular region of the probe 82 to break the temporary bond or connection between the tip 84 and the probe. The detachable tips 84 may of course be simply stored in the guidewire openings 94 so that the probe 82 or permanently attached portion of the tip may advance the transvenous tips into position outside of the guidewire 90. As described above, a controlled injury in a selected region promotes revascularization which may be further enhanced through the delivery of known angiogenic factors or various agents. It should be understood that any combination of the aforementioned detachable or micro-needle tips may be selected for a probe, and more than one probe may be deployed and operate cooperatively to penetrate blood vessel walls to carry out any object of the invention.

Figure 5A:
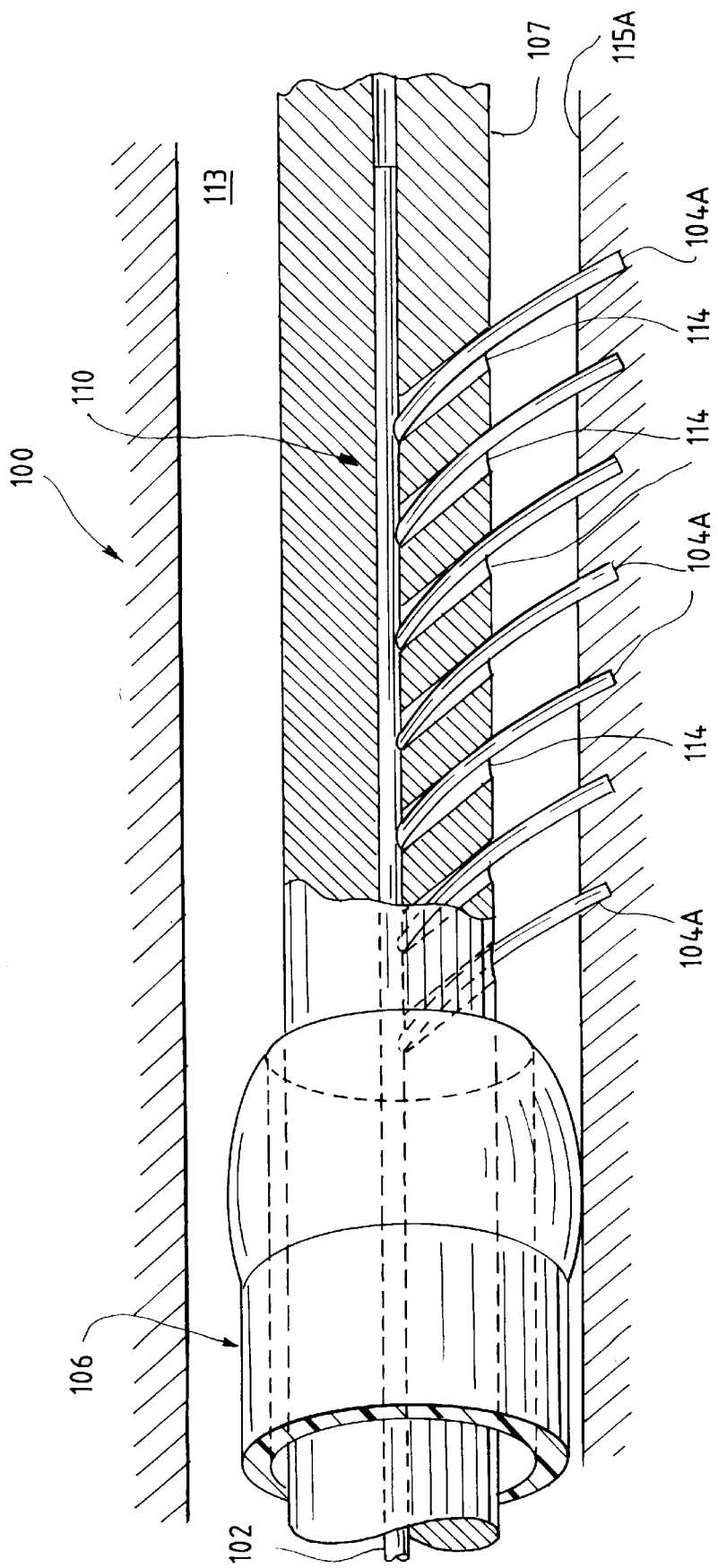
FIG. 5A–C are side views of stimulating probes deployed from a guidewire and catheter assembly that are formed with deformable and outwardly biased tips extending away from the longitudinal axis of the probe.
Figure 5B:
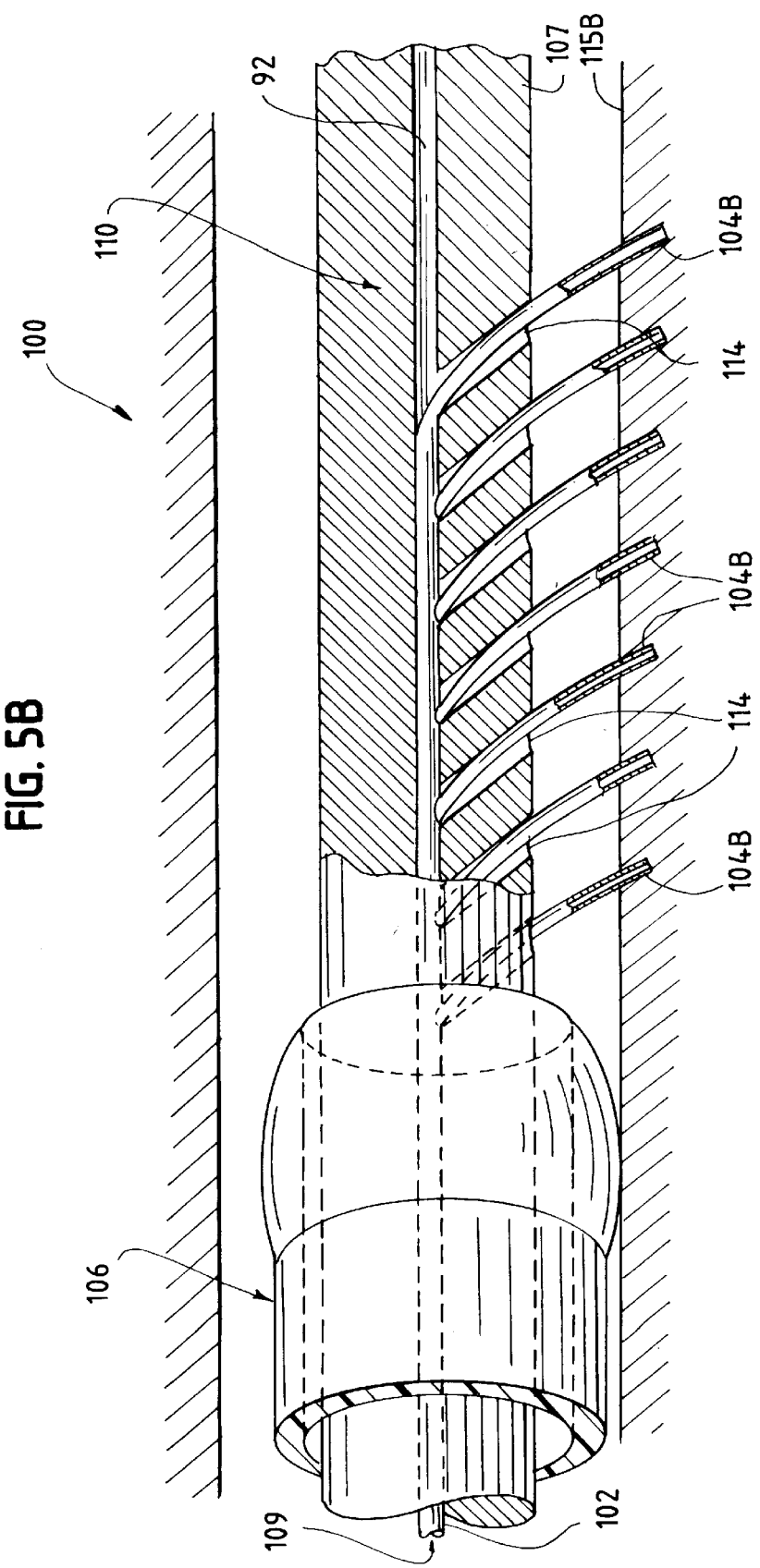
Figure 5C:
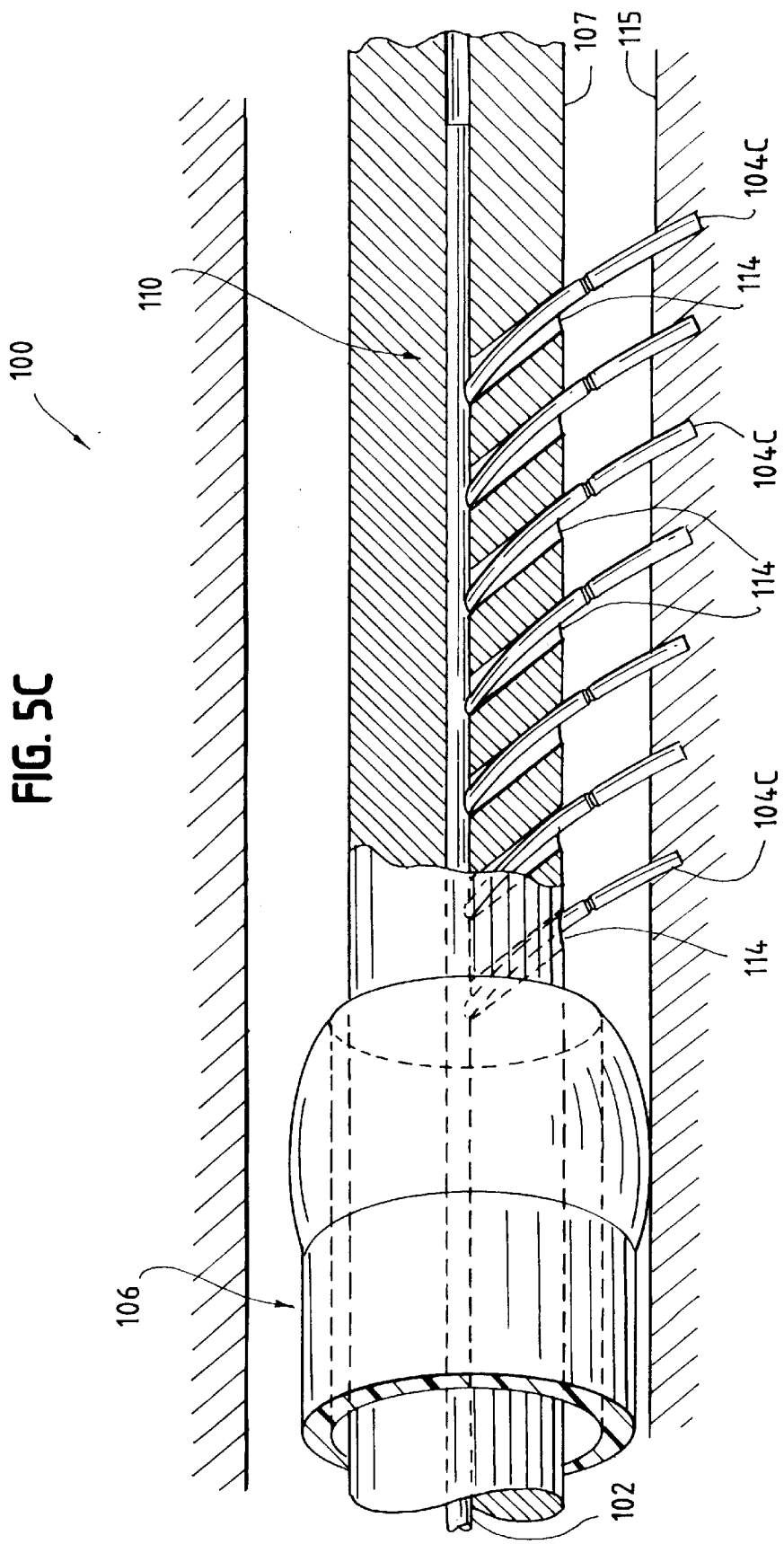

FIGS. 5A–C are illustrations of additional embodiments of the invention for stimulating selected regions and effecting drug delivery. One aspect of the present invention shown in FIG. 5A includes methods of stimulating blood vessels or muscle regions which begins with the selection of an elongated vascular probe and sheath assembly 100 wherein the vascular probe 102 is formed with a plurality of perforating members 104A to penetrate a blood vessel membrane wall 115A. A sheath covering 106 such as a catheter may be used to position the guidewire 110 and probe 102, or a guidewire alone may retain the perforating members 104A of the vascular probe in a retracted position within the outer surface 107 of the guidewire. The vascular probe and sheath assembly 100 may be inserted into a selected blood vessel 113 such as coronary vein, and the vascular probe 102 may be slidably moved in a distal direction relative to the sheath 106 to deploy the perforating members 104A of the probe beyond the outer surface 107 of the guidewire 110 and the sheath 106 to penetrate the selected blood vessel wall 115A. The stimulation may produce a localized controlled injury. The controlled injury may be augmented by the application of electrical, laser energy or any other sources of energy or stimulation in accordance with other probe embodiments described herein. The perforating members 104A of the probe 102 may be retracted thereafter by slidably moving the vascular probe in a proximal direction relative to the guidewire 110 and the sheath 106 and removed from the selected blood vessel 113. The preceding procedure may be repeated or modified as needed with the probe serving as an angiogenic vascular stimulator 102 that penetrates and stimulates the selected blood vessel wall 115A with minimal trauma while providing a net beneficial angiogenic response that promotes revascularization. Transvenous muscular revascularization may be effected when perforating members 104A of the vascular probe 102 extend through at least a portion of a venous wall towards adjacent tissue, or substantially into adjoining muscle. As a result, blood vessels such as coronary veins may be accessed with the probe so that perforating members of the probe may penetrate a selected region such as the myocardium to induce an angiogenic response that may be further enhanced with the delivery of suitable growth factors.

In accordance with yet another concept of the invention as shown in FIG. 5B, a method is provided for delivering drugs or therapeutic agents to selected body regions. An elongated delivery probe and sheath assembly 100 is initially selected wherein the delivery probe 102 is formed with a plurality of probe extensions 104B to penetrate a membrane wall 115B. The guidewire 110 and the outer sheath 106 may be configured to retain the probe extensions 104B of the probe 102 in a retracted position before deployment. After the delivery probe and sheath assembly 100 is positioned at a selected body region, the delivery probe 102 may be slidably moved in a distal direction relative to the guidewire 110 in order to deploy the extensions of the probe beyond the outer surface 107 of the guidewire. The probe extensions 104B may have various configurations including a pointed tip or any other shape to penetrate the membrane wall 115B of the selected body region. Upon delivery of the selected drug or agent, the delivery probe 102 may be retracted by slidably moving the probe in a proximal direction relative to the guidewire 110 and removed along with the sheath assembly 100 from the selected body region. A variety of other mechanisms are available for the controlled release of drugs or therapeutic agents in the apparatus and methods described herein. A fluid passageway 109 may be formed within the delivery probe 102 and the probe extensions 104B so that drugs or therapeutic agents may be administered through the fluid passageway to the selected body region. As shown in FIG. 5C, some or all of the extensions may also be formed as detachable tips 104C embedded with material to be delivered as a type of polymer matrix used in gene therapy. It should be understood that probes 102 described herein may be formed with any combination of micro-needle portions 104B, detachable tips 104C or any other type of extension from the probe. Detachable tips 104C may also be released in a variety of ways such as the passage of a current or other energy source through a wire in the probe (not shown) to permit the tip to remain at a fixed site when the probe 102 is retracted. Alternatively, the detachable tips 104C may be initially stored in sheath or guidewire openings 114, and not bonded to the probe 102, before they are simply pushed into place by the delivery probe upon penetrating a membrane wall 115C such as a blood vessel, muscle, or body organ.

The drug delivery apparatus and methods provided herein are particularly applicable for either beating or arrested heart procedures. In addition to the revascularization and drug delivery applications described herein, localized myocardial infarction may be induced by controllably reducing thickened areas of heart tissue that impede circulatory performance. The reduction or reforming of selected heart regions is achieved through known procedures such as hypertrophic cardiomyopathy or idiopathic hypertrophic subaortic stenosis. Drug delivery probe systems provided in accordance with the invention may precisely deliver reducing agents or other substances known to treat such hindrances to proper flow within the heart. A variety of drugs or therapeutic agents may be delivered in liquid or solid form to selected heart regions including alcohol, necrotic or fibrotic substances. For example, liquid agents may be injected from a proximal opening in the delivery probe 102 through a passageway 109 extending along the probe and out through extensions 104B of the probe. At the same time, therapeutic drugs may be processed in solid form or within a polymer matrix to form a probe extension or a displaced tip 104C. These and other aspects of the invention therefore provide multiple benefits in the treatment of ischemia by inducing an angiogenic response, transvascular muscular revascularization, ablation procedures or the controlled delivery of suitable reagents in the intentional reduction of muscle or selected body region. The delivery probe 102 may be modified as described herein to also direct laser energy through the probe body and extensions 104A to effect a controlled injury that reduces a thickened muscle or selected body region as in the treatment of cardiac myopathies or vascular diseases. Any or all of these procedures may be accomplished with a single or multiple embodiments of the invention, and may be effected consecutively or simultaneously according to particular applications.

Figure 6:
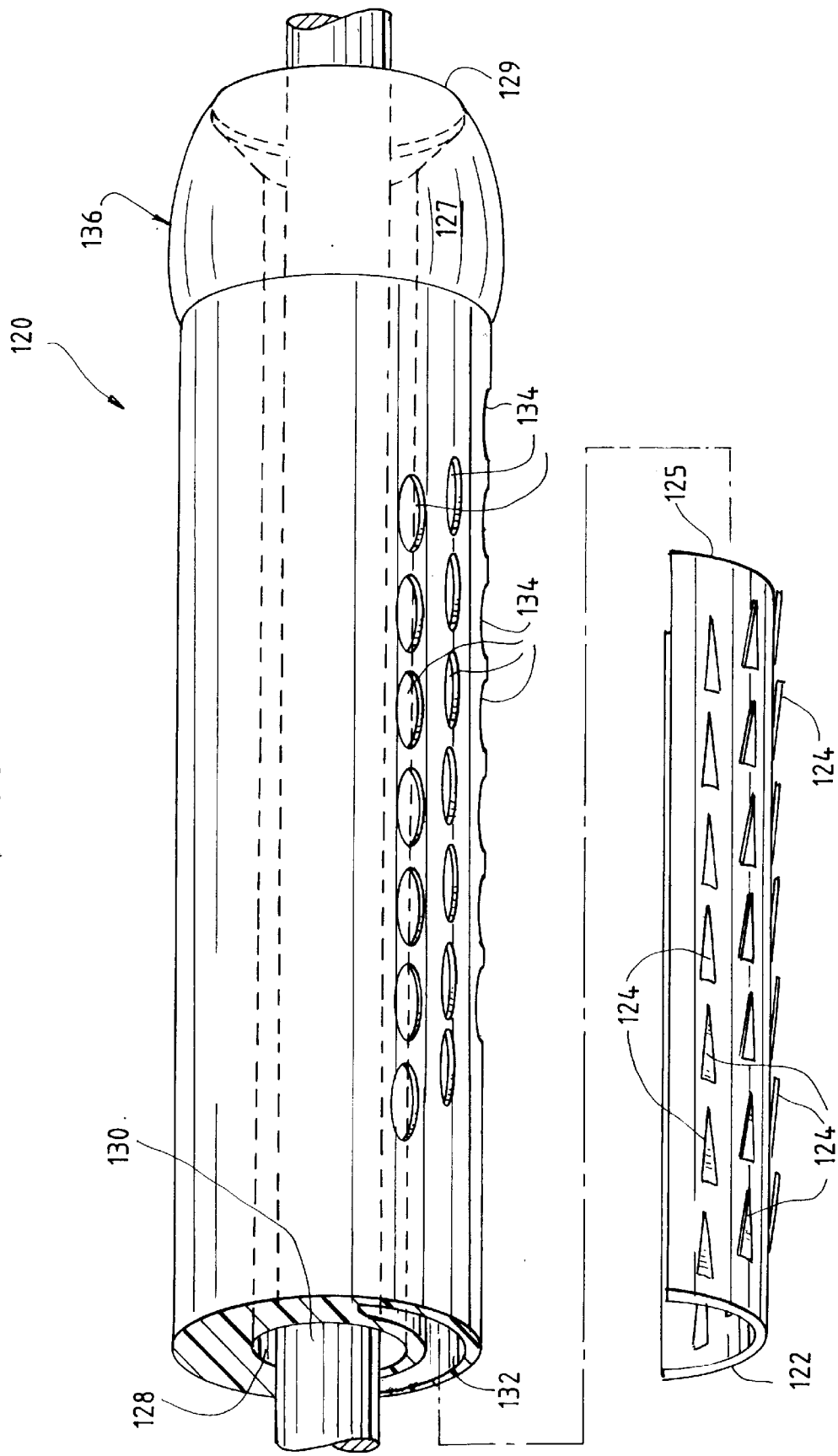
FIG. 6 is a side perspective view of a stimulating probe and sheath system that includes sharpened extensions formed along the probe that are configured to extend through perforations formed in the sheath to penetrate body membrane walls.

FIG. 6 provides an illustration of another stimulator and sheath system 120 that confers the benefits of the present invention. Although numerous probes described herein may be formed as a substantially elongated rod with spikes or sharpened perforating extensions configured to penetrate body membrane walls, the probe may be modified accordingly and have a wide variety shapes and sizes. When selected for applications within a blood vessel such as a coronary vein, the transvascular stimulating system may comprise an elongated vascular stimulator 122 having one or more perforating members 124 extending away from the stimulator for effecting a controlled injury in a selected blood vessel region that induces an angiogenic response. The stimulator 122 may have various configurations including an arcuate segment 125 that is defined by a curved surface formed with a plurality of perforating members 124 to stimulate a relatively wide region. An outer conduit 126 formed with a central passageway 132 such as a catheter or a guidewire 130 may be provided for containment of the vascular stimulator 122. The outer conduit 126 may be generally formed as a tubular sheath body or any other corresponding shape to the stimulator. At least one opening 134 may be formed in the conduit 126 that is in communication with the external conduit surface 127 that provides a passageway for at least one perforating member 124 of the vascular stimulator 122 to extend beyond the external conduit surface. Although the sheath openings 134 may be formed along its sidewall portions, an opening may be included at a distal end of the sheath for passage of one or more perforating members 124. The vascular stimulator 122 may include a distal end with a perforating member that passes through the distal sheath 129 opening to extend beyond the outer surface 127 of the sheath 126. Alternatively, the outer conduit 126 may be formed with an array of sidewall openings 134 to permit passage of the perforating members 124 of the vascular stimulator 122 beyond the external conduit surface 127. The perforating members 124 provided herein may extend away from central body of the probe 122 at various angles, and may be relatively flexible, non-flexed or outwardly biased. The apparatus 120 may be more accurately positioned with the assistance of a guidewire 130 passed through a lumen 128 in the outer sheath 126, and the inflation of a fixing balloon (not shown) to maintain its relative position within a vascular site.

The probes and stimulators provided herein may be modified to provide a controlled injury with either a mechanical device, an energy source, or a combination of both. A wide variety of available apparatus may be modified in accordance with the various aspects of the invention to provide stimulation or a controlled injury to different areas of the body. For example, existing laser apparatus may be modified in accordance with the invention for providing a controlled laser or thermal injury to a venous blood vessel and adjoining muscle region. These devices which may be modified include systems used for intravascular percutaneous procedures such as transmyocardial revascularization or cardiomyopathy, or any available laser apparatus configured for ablation of selected areas such as diseased arterial wall sections. In addition, other ablation apparatus or catheter systems employing pressurized fluid or the release of stimulating or reducing agent within a selected blood vessel or organ may all be modified in accordance with the invention to provide a type of controlled mechanical injury that induces an angiogenic response or localized ablation. Although many stimulators or probes provided herein are formed with extensions that physically penetrate a tissue membrane, a controlled injury may be effected without intimate contact at all with the membrane. Various amounts of energy may be controllably released in a selected body region in the form of laser, radio frequency, ultrasonic, or microwave energy which may be delivered from a proximal source to a relatively distal site. The extent or depth of the intended injury may be regulated by applying predetermined amounts of energy for a particular device. For example, lasers such as $CO_2$ surgical lasers, Hom-YAG or Excimer lasers for transmyocardial revascularization procedures may be modified in accordance with the invention to provide a select discharge of light energy through a blood vessel wall and adjoining muscle depending upon the strength and type of the laser, i.e., 25 to 850 watt power output range, pulse energy (J), selected wavelength. Estimates of penetration through various blood vessels and muscles may be predetermined with selected infrared or ultraviolet lasers and other energy transmissive devices. Furthermore, the placement and deployment of these angiogenic or ablating stimulators may be regulated with depth regulators described herein that may be proximally positioned along the stimulator. Rather than damaging heart tissue by forming channels directly through the myocardium with only relatively high dosages of energy, revascularization may be achieved by inducing an angiogenic response with or without physical penetration, and the application of a predetermined amount of energy that results in the spontaneous growth of new blood vessels to affected areas of the heart. In this manner, the consequences of a mechanical or a thermal energy injury may be mitigated or balanced by a positive angiogenic respond or revascularization. Although the controlled injury may be applied to the organ itself or through arterial blood vessels, relatively easy access may be provided through the venous system with minimal complications as described above.

As shown in FIG. 7, a transvascular stimulator 140 with a depth regulator such as those described herein may be provided in accordance with the concepts of the invention. The regulator (not shown) controls the extent of penetration and injury of a blood vessel 143 and 145 and muscle region 147 with a mechanical device, an energy source, or combination of both. It should be observed, however, that a muscle region 147 may be accessed through other alternate routes besides an arterial 145 or venous 143 blood vessel. For example, a muscular revascularization device may be provided that includes a muscular stimulator 142 having one or more penetrating members 144 extending away from the stimulator for penetrating a muscle membrane 148, and a depth regulator for controlling the extent of penetration of a penetrating member through the muscle membrane. An outer sheath 146 may retain the muscular stimulator 142 and assist in the selective deployment of the penetrating members 144 of the stimulator. The revascularization device 140 may further include energy transfer means in communication with the muscular stimulator as explained in FIG. 2B for effecting a controlled injury to a selected muscle region 147 with directed energy through at least one penetrating member 144 of the stimulator 142. As described above, the muscular stimulator 142 and some of its penetrating members 144 may form a multi-pronged probe. An aperture along the outer sheath 146 may also provide for slidable movement of the depth regulator (not shown) of the stimulator to provide a variable extent of penetration through the muscle membrane 148 to an appropriate depth as needed. The resulting controlled injury may be substantially proportional to the level of penetration and degree of stimulation that induces a beneficial angiogenic response and revascularization of the selected region. Another embodiment of the invention provides a transvascular muscular revascularization device 140 that comprises an elongated vascular stimulator 142 with energy transfer means for effecting a controlled injury to a selected blood vessel 143 and 145 and adjoining muscle region 147 with minimal trauma. The controlled injury to the blood vessel and its surrounding area initiates a beneficial angiogenic response and revascularization of the selected region. Although the application of energy to the selected region may not require stimulator extensions 144, penetrating members may be added to the stimulator 142 to further direct energy from the energy transfer means into the selected blood vessel wall 143 and 145 towards a muscle region 147. A stimulator sheath covering 146 such as a catheter or guidewire may be included to assist in retaining, positioning and deploying the stimulator 142. The stimulator 142 may further include a depth regulator for selectively controlling deployment of the penetrating members of the stimulator beyond the sheath 146. As shown in FIG. 7, the stimulator extensions 144 have the same or different length depending upon certain applications and the variable degree of stimulation or controlled injury. Moreover, one or more stimulators 142 may be selected within at least one sheath if desired, and their respective extensions may be aligned relative to the longitudinal axis of the sheath or located in various arrangements about the periphery of the sheath. Accordingly, the extent of any penetration by the stimulator and its energy directing components may be regulated by the initial displacement of a penetrating extension 144 of the stimulator 142 into a vascular wall 143 and 145, muscle 147 or both, and the additional release of a predetermined amount of energy from a source such as a laser. The controlled injury may be effected as a function of depth of mechanical penetration through a muscle membrane or vascular wall, if at all, and the amount of transmitted energy to that region.

While the present invention has been described with reference to the aforementioned applications, this description of the preferred embodiments and methods is not meant to be construed in a limiting sense. The aforementioned is presented for purposes of illustration and description. It shall be understood that all aspects of the invention are not limited to the specific depictions, configurations or relative proportions set forth herein which depend upon a variety of conditions and variables. The description is not intended to be exhaustive or to limit the invention to the precise forms disclosed. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications or variations of the described embodiments as falling within the true spirit and scope of the invention.

What is claimed is:

1. A method for promoting muscular revascularization while initiating an angiogenic response through a controlled injury and stimulation to selected muscle and blood vessels, comprising the following steps of:

selecting an elongated vascular probe and sheath assembly having a vascular probe defined by a longitudinal axis and a plurality of perforating members that are substantially aligned and formed along the longitudinal axis of the probe to penetrate a selected muscle and blood vessel membrane wall, and a sheath formed with an outer surface having a plurality of substantially aligned apertures, wherein the perforating members of the vascular probe are retained in a retracted position within the outer surface of the sheath and configured to selectively pass through the substantially aligned apertures of the sheath;

introducing the vascular probe and sheath assembly into the selected blood vessel;

slidably moving the vascular probe in a distal direction relative to the sheath to deploy the perforating members of the probe through the apertures of the sheath beyond the outer surface of the sheath to penetrate and stimulate the selected muscle and blood vessel wall with minimal trauma while providing a net beneficial angiogenic response that promotes revascularizaiton by effecting a localized controlled injury to the muscle and blood vessel and thereby effect angiogenesis;

retracting the perforating members of the probe by slidably moving the vascular probe in a proximal direction relative to the sheath; and removing the vascular probe and sheath assembly from the selected muscle and blood vessel, wherein the vascular probe comprises an angiogenic vascular stimulator.

2. The method as recited in claim 1 wherein the selected body region is a venous blood vessel.

3. The method as recited in claim 1 wherein the perforating members of the vascular probe extends through the blood vessel wall towards adjacent tissue.

4. The method as recited in claim 3 wherein the blood vessel wall is a coronary blood vessel and the adjacent tissue is the myocardium.

5. The method as recited in claim 1 wherein the sheath is a guidewire.

6. The method as recited in claim 1 wherein the sheath is a catheter.

7. The method as recited in claim 1 wherein a fluid passageway is formed within the probe, and further comprising the step of administering drugs, therapeutic agents or gene factors through the fluid passageway to a selected body region adjacent the selected muscle and blood vessel.

* * * * *